United States Patent
Canfield et al.

(10) Patent No.: US 12,383,236 B2
(45) Date of Patent: Aug. 12, 2025

(54) ULTRASOUND SYSTEM WITH DEEP LEARNING NETWORK PROVIDING REAL TIME IMAGE IDENTIFICATION

(71) Applicant: KONINKLIJKE PHILIPS N.V., Eindhoven (NL)

(72) Inventors: Earl M. Canfield, Snohomish, WA (US); Robert Gustav Trahms, Edmonds, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1953 days.

(21) Appl. No.: 15/782,923

(22) Filed: Oct. 13, 2017

(65) Prior Publication Data

US 2018/0103912 A1    Apr. 19, 2018

Related U.S. Application Data

(60) Provisional application No. 62/410,000, filed on Oct. 19, 2016.

(51) Int. Cl.
*A61B 8/00* (2006.01)
*A61B 8/06* (2006.01)
*A61B 8/08* (2006.01)
*A61B 8/14* (2006.01)

(52) U.S. Cl.
CPC ............. *A61B 8/5223* (2013.01); *A61B 8/06* (2013.01); *A61B 8/0883* (2013.01); *A61B 8/14* (2013.01); *A61B 8/461* (2013.01); *A61B 8/488* (2013.01); *A61B 8/5253* (2013.01)

(58) Field of Classification Search
CPC ... A61B 5/7267; A61B 8/0883; A61B 8/5253; A61B 8/5223; A61B 8/461; A61B 8/4494; A61B 8/06; A61B 8/488; A61B 8/14; A61B 8/0891; G16H 50/30
See application file for complete search history.

(56) References Cited

U.S. PATENT DOCUMENTS 5,315,999 A  *  5/1994  Kinicki ............... A61B 8/467
                                              600/443
5,579,768 A  †  12/1996  Klesenski
5,833,613 A      11/1998  Averkiou et al.
(Continued)

FOREIGN PATENT DOCUMENTS

WO       2015/058044 A1  †  4/2015

OTHER PUBLICATIONS

Chen et al. Iterative Multi-domain Regularized Deep Learning for Anatomical Structure and Detection and Segmentation from Ultrasound Images. MICCAI 2016, Part II, LNCS 9901, pp. 487-495. DOI: 10.1007/978-3-319-46723-8_56 , Oct. 2, 2016(Year: 2016).*

(Continued)

*Primary Examiner* — Christopher Koharski
*Assistant Examiner* — Younhee Choi

(57) ABSTRACT

An ultrasound system with a deep learning neural net feature is used to automatically identify image anatomy or pathology and the view of the anatomy seen in the image. The feature also can assess image quality in real time. Based on identified anatomy, the system can automatically annotate images, launch measurement tools and exam protocols, and perform image control adjustments to aid diagnosis and improve exam workflow.

7 Claims, 3 Drawing Sheets

(56) References Cited

U.S. PATENT DOCUMENTS

| | | | |
|---|---|---|---|
| 5,997,479 | A | 12/1999 | Savord et al. |
| 6,013,032 | A | 1/2000 | Savord |
| 6,443,896 | B1 | 9/2002 | Detmer |
| 6,530,885 | B1 | 3/2003 | Entrekin et al. |
| 6,623,432 | B2 | 9/2003 | Powers et al. |
| 2007/0055153 | A1* | 3/2007 | Simopoulos .......... G16H 30/40 600/437 |
| 2017/0143312 | A1* | 5/2017 | Hedlund ................ A61B 6/037 |
| 2017/0262982 | A1* | 9/2017 | Pagoulatos .......... G06K 9/4628 |
| 2017/0360412 | A1* | 12/2017 | Rothberg ................ G06T 11/60 |
| 2018/0071452 | A1* | 3/2018 | Sharma ................ A61M 5/007 |

OTHER PUBLICATIONS

Brebisson, "Deep Neural Networks for Anatomical Brain Segmentation", (entire article submitted—no page numbers), published 2015, Publisher: IEEE, 2015 IEEE Conference on Computer Vision and Pattern Recognition Workshops (CVPRW).†

Chen, "Iterative Multi-Domain Regularized Deep Learning for Anatomical Structure Detection and Segmentation from Ultrasound Images", entire article submitted (pp. 487-495), published Oct. 2, 2016, Publisher: Springer, MICCAI 2016 Lecture Notes in Computer Science, vol. 9901.†

Baumgartner, "Real-Time Standard Scan Plane Detection and Localisation in Fetal Ultrasound Using Fully Convolutional Neural Networks", entire article submitted (pp. 203-211), published Oct. 2, 2016, Publisher: Springer, MICCAI 2016 Lecture Notes in Computer Science, vol. 9901.†

\* cited by examiner
† cited by third party

ULTRASOUND SYSTEM WITH DEEP LEARNING NETWORK PROVIDING REAL TIME IMAGE IDENTIFICATION

CROSS-REFERENCE TO PRIOR APPLICATIONS

This application claims the benefit of or priority of U.S. Provisional patent application Ser. No. 62/410,000, filed Oct. 19, 2016, all of which is incorporated herein in whole by reference.

This invention relates to medical diagnostic ultrasound systems and, in particular, to ultrasound systems with deep learning networks which provide real time image identification and system setup.

Currently available medical ultrasound systems enable clinicians to conduct ultrasound scans on a patient using on-board exam protocols, capture images, make measurements and use built-in algorithms and report generation software to make diagnoses and report the results of a diagnosis. Prior to starting the exam, the clinician must set up the system by selecting the settings and functions to be used and performed during the exam. This usually starts with selecting the probe type to be used, then the exam type (OB, cardiology, peripheral vascular, etc.), followed by an exam protocol when one is to be used, and other ultrasound machine operating settings. In the past, system setup took a considerable amount of time, as an ultrasound machine typically has scores of different controls and thousands of settings. This burden was eased considerably when ultrasound systems became able which save settings used in one exam for automatic setup of a similar later exam. See, for instance, U.S. Pat. No. 5,315,999 (Kinicki et al.) Ultrasound systems able to save and recall system presets enabled the clinician to save his or her preferred settings for specific types of ultrasound exams, then recall them for use in a future exam. The manufacturers of these systems evolved this feature into systems having what are known as "tissue specific presets." These are factory-installed presets typically used in the various types of ultrasound exams which can be invoked on the system by pressing a single button. For instance, an obstetrician preparing to perform a fetal exam of an expectant mother can press the "OB" button and the ultrasound system is immediately conditioned with settings typically used for the performance of a fetal exam.

It is desirable to advance such automation of setting up an ultrasound system for a particular exam even further. One branch of evolving artificial intelligence which shows promise is "deep learning." Deep learning is a rapidly evolving branch of machine learning algorithms that mimic the functioning of the human brain in analyzing problems. The human brain recalls what was learned from solving a similar problem in the past, and applied that knowledge to solve a new problem. Exploration is underway to ascertain possible uses of this technology in a number of areas such as pattern recognition, natural language processing and computer vision. Deep Learning algorithms have a distinct advantage over traditional forms of computer programming algorithms in that they can be generalized and trained to recognize image features by analyzing image samples rather than writing custom computer code. The anatomy visualized in an ultrasound system would not seem to readily lend itself to automated image recognition, however. Every person is different, and anatomical shapes, sizes, positions and functionality vary from person to person. Furthermore, the quality and clarity of ultrasound images will vary even when using the same ultrasound system. That is because body habitus will affect the ultrasound signals returned from the interior of the body which are used to form the images. Scanning an organ through thick layers of body fat will result in greatly attenuated ultrasound signals and poorly defined anatomy in the images. Accordingly it is desirable to use deep learning in an ultrasound system in a manner which is effective for a wide patient population in order to expedite ultrasound exams through ultrasound image recognition.

It is an object of the present invention to use deep learning technology to recognize anatomy in ultrasound images.

It is a further object to recognize, not just anatomy, but the view of the anatomy in ultrasound images.

It is a further object to use deep learning recognition of anatomy to automate ultrasound system setup for an ultrasound exam.

In accordance with the principles of the present invention an ultrasound system and method are described which enable an ultrasound system to identify anatomy in an image through processing by a neural network model. The neural network model is first trained by presenting to it a plurality of images of known anatomy. Once trained, live images acquired by a user are analyzed by the neural net model in real time, which identifies the anatomy in the images. The identification of the anatomy is used to annotate the image, or set up the user controls on the ultrasound system for the conduct of an exam of the identified anatomy.

IN THE DRAWINGS

Figure 1:
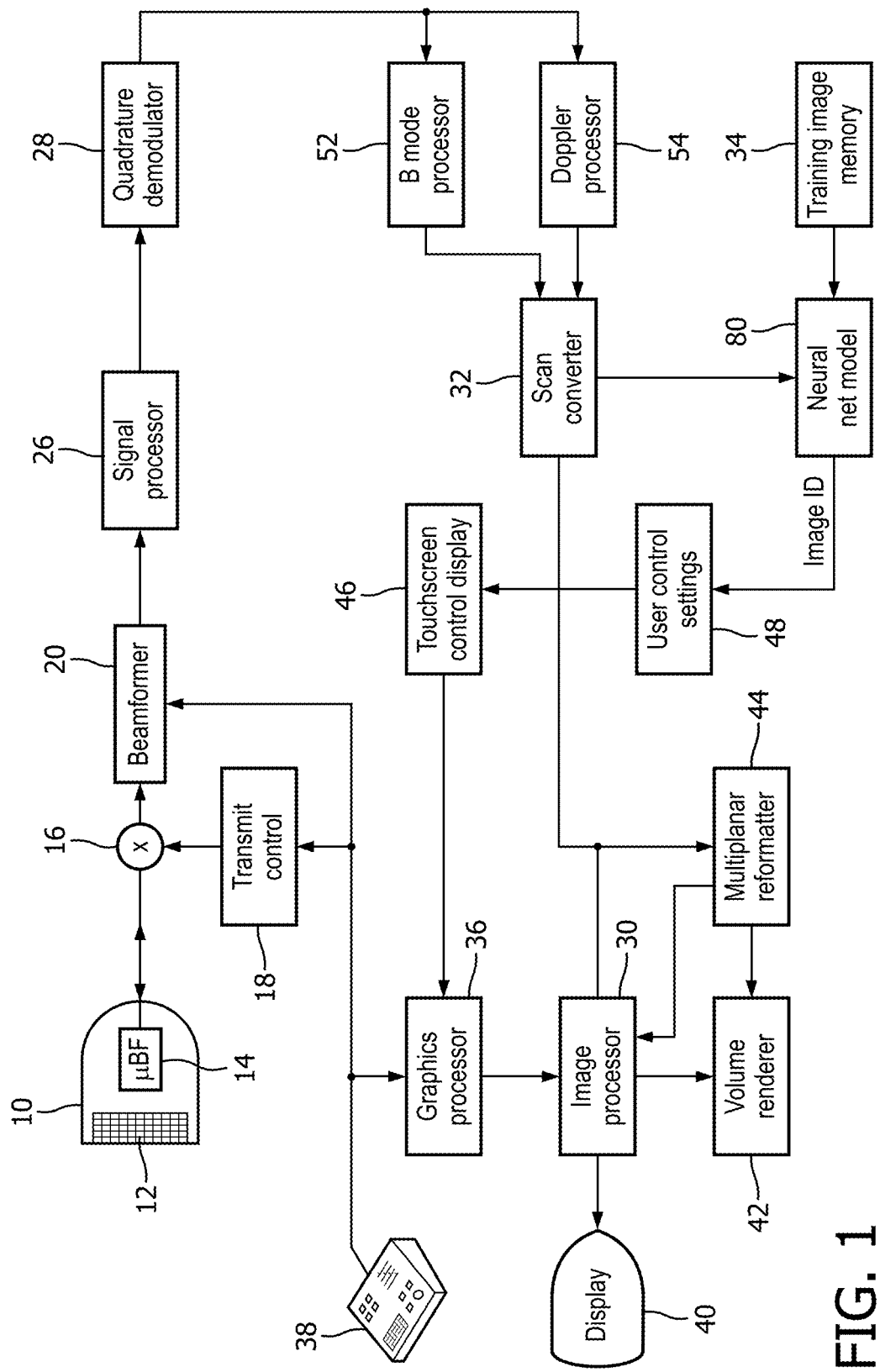
FIG. 1 illustrates an ultrasound system configured in accordance with the principles of the present invention.

Referring now to FIG. 1, an ultrasonic diagnostic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to a microbeamformer 14 in the probe which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a transmit controller 18 coupled to the T/R switch and the beamformer 20, which receives input from the user's operation of the user interface or control panel 38. Among the transmit characteristics controlled by the transmit controller are the amplitude, phase, and polarity of transmit waveforms. Beams formed in the direction of pulse transmission may be steered straight ahead from (orthogonal to) the transducer array, or at different angles for a wider field of view.

The echoes received by a contiguous group of transducer elements are beamformed by appropriately delaying them and then combining them. The partially beamformed signals produced by the microbeamformer 14 from each patch are coupled to a main beamformer 20 where partially beamformed signals from individual patches of transducer elements are combined into a fully beamformed coherent echo signal. For example, the main beamformer 20 may have 128 channels, each of which receives a partially beamformed signal from a patch of 12 transducer elements. In this way the signals received by over 1500 transducer elements of a two-dimensional array can contribute efficiently to a single beamformed signal.

The coherent echo signals undergo signal processing by a signal processor 26, which includes filtering by a digital filter and noise reduction as by spatial or frequency compounding. The signal processor can also shift the frequency band to a lower or baseband frequency range. The digital filter of the signal processor 26 can be a filter of the type disclosed in U.S. Pat. No. 5,833,613 (Averkiou et al.), for example. The processed echo signals then are demodulated into quadrature (I and Q) components, which provide signal phase information.

Figure 2:
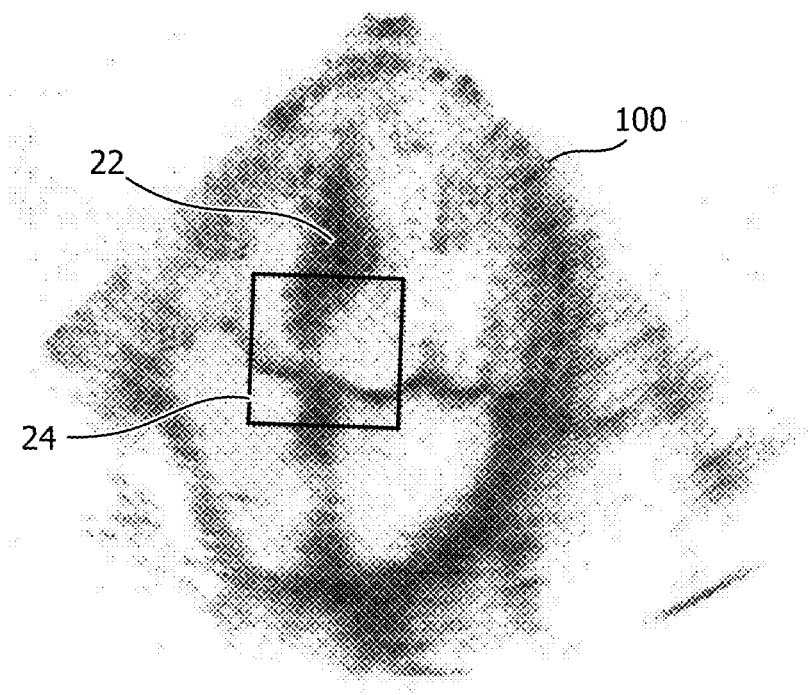
FIG. 2 illustrates an ultrasound image showing a four-chamber view of a heart.

The beamformed and processed coherent echo signals are coupled to a B mode processor 52 which produces a B mode tissue image. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 54, which stores ensembles of echo signals from discrete points in an image field which are then used to estimate the Doppler shift at points in the image with a fast Fourier transform (FFT) processor. For a color Doppler image, the estimated Doppler flow values at each point in a blood vessel are wall filtered and converted to color values using a look-up table. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format as shown in FIG. 2. Either the B mode image or the Doppler image may be displayed alone, or the two shown together in anatomical registration in which the color Doppler overlay shows the blood flow in tissue and vessels in the image.

The ultrasound images produced by the scan converter 32 are coupled to an image processor 30 and a multiplanar reformatter 44. The multiplanar reformatter converts echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled to an image processor 30 for further enhancement, buffering and temporary storage for display on an image display 40. A graphic display overlay containing textual and other graphic information such as patient ID is produced by a graphics processor 36 for display with the ultrasound images.

In accordance with the principles of the present invention the ultrasound system includes a neural network model 80, the software of which is stored in a digital memory. Deep learning neural net models comprise software which may be written by a software designer, and are also publicly available from a number of sources. An application which can be used to build a neural net model called "NVidia Digits" is available at https://developer.nvidia.com/digits. NVidia Digits is a high level user interface around a deep learning framework called "Caffe" which has been developed by the Berkley Vision and Learning Center, http://caffe.berkeleyvision.org/. A list of common deep learning frameworks suitable for use in an implementation of the present invention is found at https://developer.nvidia.com/deep-learning-frameworks. Coupled to the neural net model 80 is a training image memory 34, in which ultrasound images of known patient anatomy are stored and used to train the neural net model to identify ultrasound images of that anatomy. Live images produced by the ultrasound system of FIG. 1, such as the heart image 100 of FIG. 2, are presented to the neural net model after training for identification of the anatomy in the images by the model. In a constructed implementation of the present invention, the neural net model was trained to identify not only the anatomy in an ultrasound image, but also the view of the anatomy seen in the ultrasound image, e.g., a heart in either a two-chamber view, a three-chamber view, or a four-chamber view; or a carotid artery in either a long axis view or a short axis view. The ultrasound image 100 of FIG. 2 is a four-chamber view of a heart. The trained neural net model produces this information as its Image ID, and also produces a confidence factor of what the model estimates as the accuracy of its identification, e.g., 80% confident, 100% confident, or some other factor. When the neural net model is 100% confident in its identification, the Image ID is coupled to a user control settings controller 48 of the ultrasound system, where settings of the system for an exam of the identified type of anatomy are established. These settings are applied to a touchscreen display control 46, where the graphics of a touchscreen user control display are modified accordingly and coupled to the graphics processor 36. The graphics processor generates the appropriate control graphics, which are applied to a touchscreen display 60 (FIG. 3) on the user control panel 38 of the ultrasound system.

Figure 3:
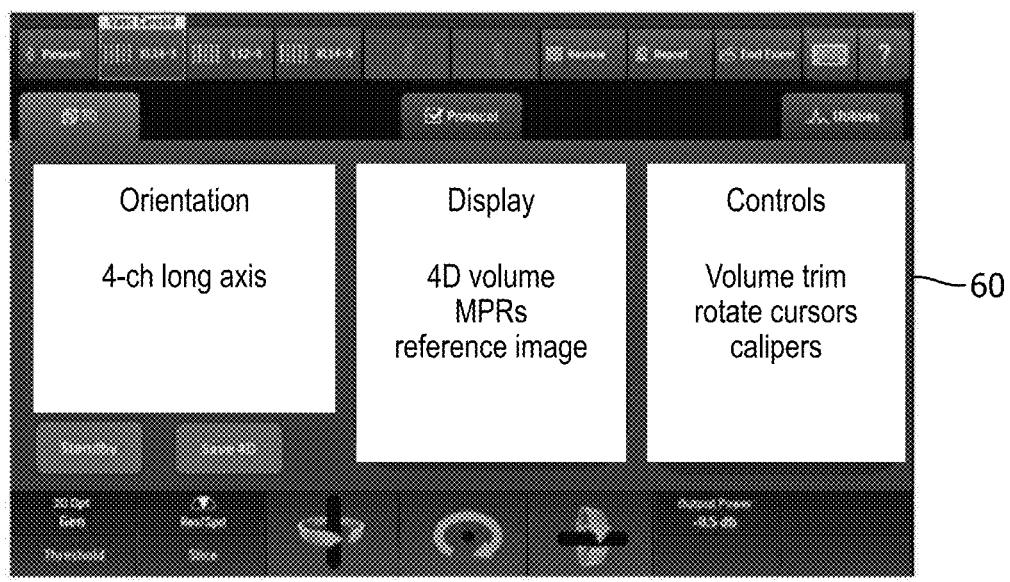
FIG. 3 illustrates a touchscreen user control panel of an ultrasound system which has been set up for an ultrasound exam in response to identification of the anatomy in an ultrasound system by a neural network model.

FIG. 3 illustrates an example of touchscreen control panel 60. In this example the neural net model 80 has analyzed ultrasound image 100 of FIG. 2 and identified it as a four-chamber view of the heart. This identity (Image ID) is applied to the user control settings 48, where the appropriate settings for a cardiac exam using a four-chamber heart view are invoked on the ultrasound system. The ultrasound system is thus automatically set up for this exam. The settings are coupled to the touchscreen display control, where the appropriate display for the touchscreen display 60 is generated and applied to the touchscreen display panel by the graphics processor 36. As seen in FIG. 3, the "3D" tab on the display is shown, since the exam for which the system is set up will acquire and use 3D volume images. In the "Orientation" box on the left the touchscreen shows the identified view, the "4-ch long axis" view. The ultrasound probe 10 is oriented for this view. The center "Display" box shows the types of ultrasound images that will be produced and displayed on the display for the exam, which in this example comprise a 4D (live) volume image, MPR image planes produced by the multiplanar reformatter 44, and a reference image of the four chambers. The "Controls" box on the display shows that three user control have been made active for the exam by the user control setting 48, a volume trim control, the rotation cursors (seen at the bottom of the display), and a calipers for measurement. In FIG. 2 a calipers graphic 24 has been placed over the central myocardial wall 22 of the heart for measurement of myocardial wall thickness.

Figure 4:
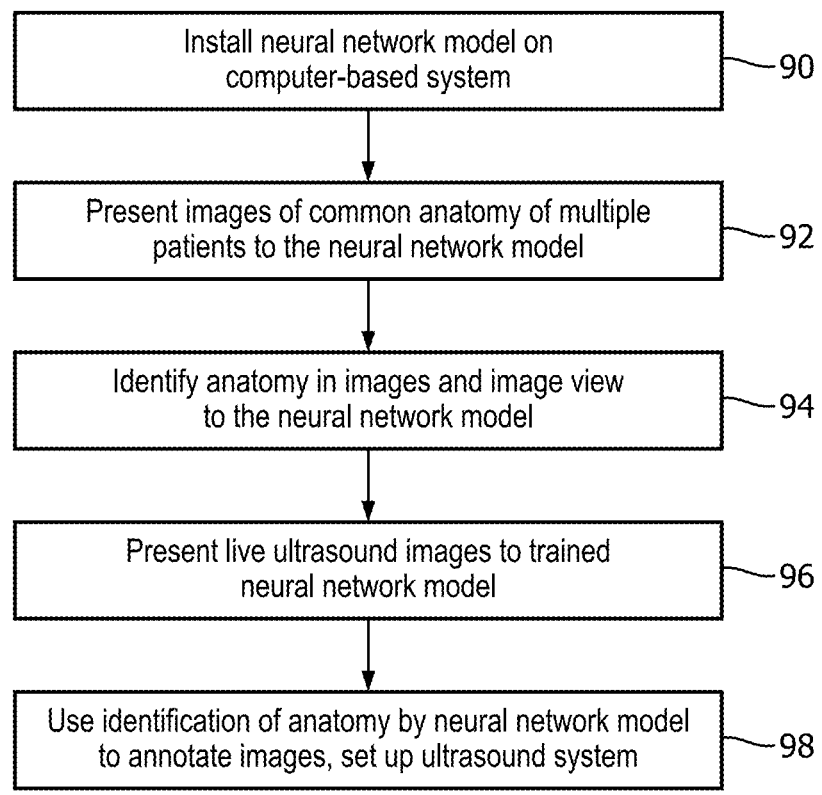
FIG. 4 illustrates a method for training a neural network model for an ultrasound system and using the model to identify anatomy in ultrasound images and set up an ultrasound system.

A method for training and using a neural network model to identify the anatomy in ultrasound images is shown in FIG. 4. In step 90, a neural network model is installed on a computer-based system. The neural network model may be one designed by a software architect, or may be one built using one of the deep learning frameworks available as described above. In step 92 images of the same anatomy acquired from a plurality of patients are presented to the neural network model to train it to identify the anatomy, along with the known type of the anatomy and its view in the images in step 94. The number of training images used is preferably in the hundreds or thousands in order to train the neural network model in the variations of such anatomy. With the trained neural network model installed on an ultrasound system, images acquired by the ultrasound system are presented to the neural network model in step 96 for identification. In step 98 the identification produced by the neural network model is used to annotate the images, e.g., as a four-chamber view or a short axis view, and is also used to set up the ultrasound system for an exam as described above.

Variations of the system and method described above will readily occur to those skilled in the art. An ultrasound system can use deep learning models to assess image quality and give feedback to the clinician, prompting the clinician to acquire better resolved images where possible. Exam protocols on the ultrasound system can be changed dynamically based on automatically-identified anatomy or pathology. As anatomy is recognized, exam protocols can automatically advance or change. Diagnostic decision support can be implemented by combining previous patient history information, anatomy identification, and anatomy measurements. This data can be processed by deep learning algorithms to provide diagnostic decision support results, confirming a diagnosis.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, for example, the deep learning software modules, or components and controllers therein, also may be implemented as part of one or more computers or microprocessors. The computer or processor may include a computing device, an input device, a display unit and an interface, for example, for accessing the Internet as shown in FIG. 1. The computer or processor may include a microprocessor. The microprocessor may be connected to a communication bus, for example, to access a PACS system or the data network for importing training images. The computer or processor may also include a memory. The memory devices such as the image memory 28 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and transmission of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a neural network model module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic diagnostic imaging system for identifying anatomy in ultrasound images using deep learning comprising:
    an ultrasound probe adapted to acquire live ultrasound image signals;
    an image processor, coupled to the probe, which is adapted to produce ultrasound images;
    a neural network model stored in a non-transitory computer-readable memory and adapted to receive the ultrasound images and to identify anatomy in the ultrasound images through a deep learning technique;
    a user control settings controller coupled to the neural network model, the settings controller configured to obtain imaging system settings and activate user controls for an exam of the identified anatomy in response to the identification of the anatomy by the neural network model; and
    a display adapted to display the ultrasound images, the system settings, and the identified anatomy.

2. The ultrasonic diagnostic imaging system of claim 1, wherein the neural network model is further adapted to identify a view of the anatomy of an ultrasound image.

3. The ultrasonic diagnostic imaging system of claim 2, wherein the identified view is one of a two-chamber view, a three-chamber view, a four-chamber view, a long axis view, or a short axis view.

4. The ultrasonic diagnostic imaging system of claim 1, wherein the display is adapted to display the user controls activated in response to the identification of the anatomy by the neural network model.

5. The ultrasonic diagnostic imaging system of claim 1, further comprising a training image memory storing training images for the neural network model.

6. The ultrasonic diagnostic imaging system of claim 1, wherein the display is further adapted to display ultrasound images annotated with the identified anatomy in response to the identification of the anatomy by the neural network model.

7. The ultrasonic diagnostic imaging system of claim 6, wherein the display is further adapted to display ultrasound images annotated with activated user control graphics in response to the identification of the anatomy of the ultrasound images by the neural network model.

\* \* \* \* \*